United States Patent [19]

Kuhl

[11] 4,439,186

[45] Mar. 27, 1984

[54] DILATION DEVICE

[76] Inventor: Adolf Kuhl, Finkenhof 3b, D-3000 Hannover 61, Fed. Rep. of Germany

[21] Appl. No.: 408,831

[22] Filed: Aug. 17, 1982

[30] Foreign Application Priority Data

Sep. 29, 1981 [DE] Fed. Rep. of Germany ....... 3138620

[51] Int. Cl.³ .................... A61M 25/00; A61B 19/00
[52] U.S. Cl. ..................................... 604/99; 128/1 D
[58] Field of Search ................. 128/344, 1 D; 604/97, 604/98, 99

[56] References Cited

U.S. PATENT DOCUMENTS

| 3,720,199 | 3/1973 | Rishton et al. | 609/98 |
| 3,769,960 | 11/1973 | Robinson | 128/1 D |
| 4,154,227 | 5/1979 | Krause | 128/1 D |

*Primary Examiner*—Stephen C. Pellegrino
*Attorney, Agent, or Firm*—Merriam, Marshall & Bicknell

[57] ABSTRACT

A dilation device for dilating or blocking vessels and other body cavities with a catheter having an expandable element. The expandable element is a balloon-type dilation element having a pressure volume relationship which is non-linear. A pressure source is provided which supplies a pulsating pressure to the expandable element for alternating expansion and contraction of said element.

8 Claims, 3 Drawing Figures

DILATION DEVICE

This invention relates to a dilation device for dilating or blocking vessels and other body cavities with a catheter which can be connected to a pressure source, said catheter having an expandable or dilatable element.

BACKGROUND OF THE INVENTION

It has been known to open or expand, or to block, respectively, vessels and other cavities in the human body by use of inflatable catheters. To this end dilation catheters are used which have an expansion or dilation element at their end. When positioning the catheter, the dilation element is positioned at the location to be dilated and then pumped up. It is a disadvantage during pumping-up that the vessel or other body cavity in question be blocked by the dilation element because the supply of blood to the upstream or next in line organs, for example, will be interrupted for the duration of the treatment.

An object of the invention is to provide a dilation device of the above-mentioned type which permits alternating expansion and contraction of the dilation element in rhythm with the heart pulse or frequency, to free the vessel or the body cavity in question so that fluid can circulate between short-term dilation phases.

In order to satisfy this object there is provided, according to the invention, a pressure source means which supplies a pulsating pressure, the lower pressure value of which is synchronized, as an operating pressure, with the expansion characteristics of the dilation element so that it lies near but below the steep volume increase, in the area of the steep pressure increase at about a constant volume, and the upper pressure value of which lies in the area of the steep volume increase, whereby a change of the pressure p causes a defined volume change v, and in which the dilation element is so designed that its volume above the operating pressure can follow pressure pulses with a pulsing frequency of 0.5 to 3 Hz.

The invention is based on the idea that the expansion of a dilation element forming a component of a catheter normally has a delay or phase shift towards the pressure pulses of the pressure source as compared to the pressure charge by means of the pressure source, if the pressure of the source is reduced to about zero each time between two pressure pulses. This can be attributed to the flow resistance of the catheter and to the pressure-volume characteristics of a balloon-type dilation element. When the dilation element is pumped-up from a pressure-free condition, the pressure in the dilation element first increases without causing a substantial increase in volume. Only after a certain pressure, which may be called a "knee" or inflection point, does a substantial volume gradient result, that is, the volume of the dilation element greatly increases with increasing pressure. By means of the invention, the operating pressure is set to be closely beneath the inflection point of the pressure-volume curve and so that as well, a certain minimum or pre-pressure is maintained in the dilation element between pressure pulses. The increase of fluid pressure which is necessary to increase the volume of the dilation element is relatively small starting from this minimum or pre-pressure. In this way it is possible, with small pressure changes on the liquid in the catheter, to cause large volume changes in the dilation element so that the dilation element can be pumped-up or expanded in rhythm with the heart pulse or frequency and then contracted. As a result, it is not necessary to carry out a cycle consisting of pumping-up and contraction of the dilation element with each pulse beat but, instead, the dilation element can remain pumped-up and be contracted over one or several pulse beats. It is only important that the process of pumping-up and contraction takes place relatively quickly and with as low an inertia as possible.

A beneficial feature of the invention includes the provision of a catheter comprising a tube which can extend from a fluid pressure source connection to the dilation element, and with the tube having a radial expandability less than that of the dilation element. It is preferred that the diameter of the tube in a zone adjacent the dilation element be relatively small, and that the remainder of the tube, leading to the pressure source, be enlarged. This enlargement of the tube diameter, which reduces flow resistance through the catheter, together with the limited expandability of the tube increases the upper limiting frequency for transmission of pressure pulses to the dilation element. Preferably, the upper limiting frequency for the transmission of pressure pulses from the pressure source to the dilation element lies at about 100 Hz, thereby permitting higher frequency pressure fluctuations to be superimposed on the pressure pulses, which, for example, have a triangular, sawtooth-type or sinusoidal time sequence. Due to these types of fluctuations, which are superimposed on a pressure pulse, the vessel dilation is improved.

In order to make a pressure measurement possible during advancement of the catheter to the dilation location, a particularly useful catheter includes a tube with a pressure measuring channel, the front end of which extends past or beyond the dilation element. The extending portion is soft so that injuries to body cavities and vessels are avoided.

Following hereinafter is an example describing the invention in detail with reference to the attached drawings.

DETAILED DESCRIPTION OF THE DRAWINGS

Figure 1:
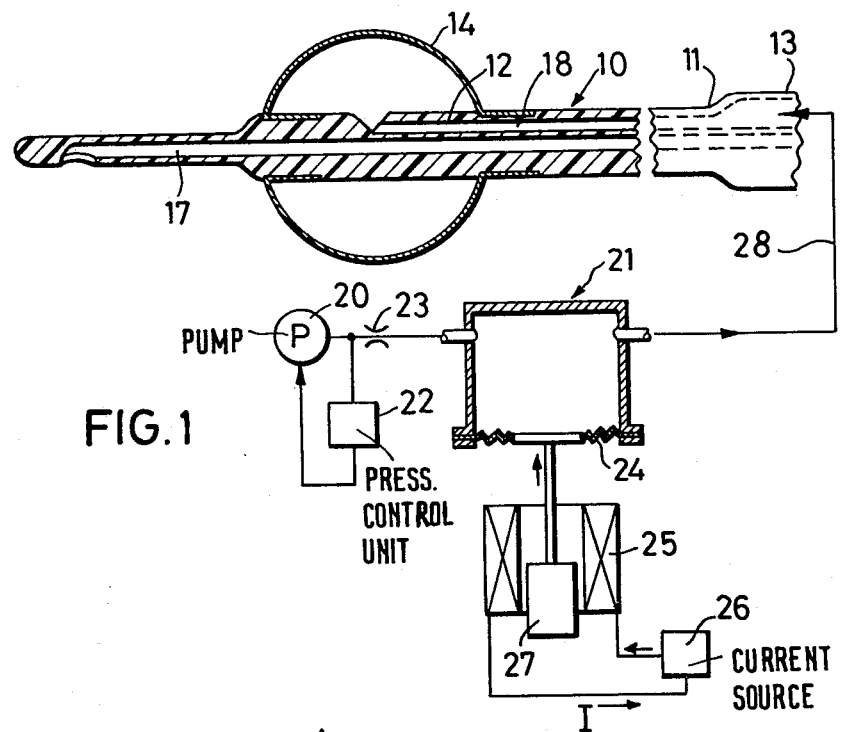
FIG. 1 is a cross-sectional view of a dilation catheter attached to a source of fluctuating pressure.

The dilation catheter 10 illustrated in FIG. 1 consists of a tube 11 having a section 12 at the end towards the patient. Section 12 has a length of 10 to 15 cm and it has a smaller diameter than the remaining portion 13 of tube 11. The tube 11 has two continuous longitudinal channels 17 and 18. The rear end of the channel 18 is connected to a pressure source. The dilation element 14 is fastened, for example by an adhesive, to the open front end of the tube section 12. The dilation element 14 consists of an expandable balloon or tubular piece which sealingly surrounds the section 12 of the catheter 10 and in which the channel 18 terminates. As a result, element 14 can be pumped-up like a balloon by the pressure in the channel 18. The ability of the dilation element 14 to expand radially is substantially greater than that of the tube 11. When a pressure is generated in the dilation catheter 10 by means of a gas or a fluid supplied to it, the tube 11 retains its diameter size, in general, while the dilation element 14 expands.

A suitable source of fluctuating pressure is also shown in FIG. 1. Pump 20 supplies a fluid, preferably a liquid, under a pressure $p_0$ to container 21, which is filled with the fluid. Control unit 22 associated with pump 20 insures that fluid pressure at the outlet of the pump is exactly maintained. Between pump 21 and container 23, a throttle point 21 is provided to isolate pressure fluctuation within the container from appearing in pump 20 and control unit 22.

Container 21 is provided with a flexible bottom 24 which is connected to a magnetic core 27 situated within the coil of electromagnet 25. Current source 26 provides a current pulse or a desired series of pulses, to electromagnet 27, causing core 27 to be drawn into the magnet, moving flexible bottom 24 into container 21 and thus producing a corresponding pressure pulse, or a series of pressure pulses, in the fluid within the container. The pressure pulses are transmitted via line 28 to dilation element 14.

The catheter 10 also has a pressure measuring channel 17 which extends forward and past the dilation element 14 towards the front end of the catheter. The pressure measuring channel 17, which is open laterally at its front end, serves to provide means to measure the pressure during advancement of the catheter 10 towards the dilation location. Channel 17 extends over the entire length of the catheter 10. The catheter 10 thus contains a double lumen, whereby the channel 18 provides means to pressurize the dilation element 14 and the channel 17 provides means to measure the pressure in the vein or vessel.

Figure 2:
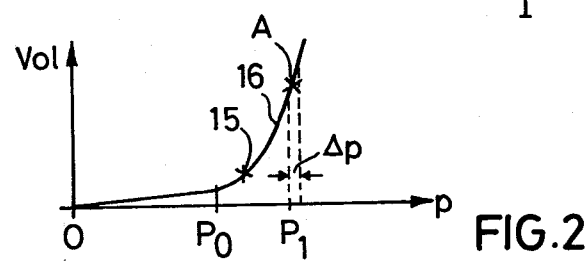
FIG. 2 is a graph showing the pressure-volume curve of the dilation element in the catheter shown in FIG. 1.

FIG. 2 illustrates the pressure-volume curve of the dilation element 14. The pressure p in the interior of the dilation element 14 is plotted on the abscissa against the volume of the dilation element on the ordinate. The volume of the dilation element 14 at first increases only slightly when the pressure p increases from the value $p_0$ up to the inflection point 15. Upon further increase of pressure p a substantial change in volume takes place, as is obvious in the curve, which shows the volume increasing rapidly with increasing pressure.

The pressure source connected to the catheter 10 is so designed that it generates pressure pulses, the lower pressure value of which corresponds to an operating pressure $p_0$ which lies below but close to the inflection point 15, while the upper pressure value $p_1$ lies on the rising branch 16 of the pressure-volume curve. High frequency pulse vibrations with a frequency of about 100 Hz can be superimposed on the pressure pulses having the higher value $p_1$, whereby a pressure increase $\Delta p$ results periodically above the value $p_1$. The value $p_1$ preferably lies at a point in the pressure-volume characteristic of the dilation element at which the curve is essentially straight, so that a given increase in pressure will reproducibly result in a uniform increase in volume. The operating point A lies in the center of the interval $\Delta p$.

Figure 3:
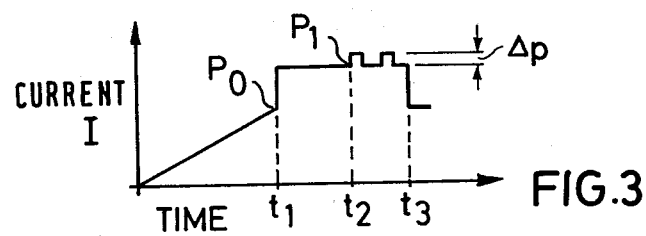
FIG. 3 is a graph showing the current supplied to the pressure source of FIG. 1 to produce a fluctuating pressure.

FIG. 3 shows a typical current wave-form, as supplied by source 26 to electromagnet 25. At time $t_1$, when the pressure in container 21 is $p_0$, a base pulse of current is supplied to electromagnet 25, causing the pressure to pass inflection point 15 and to rise to $p_1$ at time $t_2$. A series of smaller current pulses then causes the pressure to fluctuate by a value $\Delta p$, until the end of the base pulse at time $t_3$.

My copending application Ser. No. 408,832 filed Aug. 17, 1982, discloses apparatus for generating such pressure pulses and the entire disclosure of that application is incorporated herein by reference.

The foregoing detailed description has been given for clearness of understanding only and no unnecessary limitations should be understood therefrom as modifications will be obvious to those skilled in the art.

What is claimed is:

1. A dilation device for dilating or closing blood vessels and other body cavities comprising:
   a catheter having a radially expandable dilation element, said element having a volume-pressure characteristic including a first zone in which the rate of increase in volume with increasing pressure is relatively low, a second zone in which said rate is substantially higher and substantially linear, and an inflection point separating said first and second zones, and
   a source of fluid pressure connected to said catheter, control means for said fluid pressure source for producing a pulsating pressure between a lower value lying closely below said inflection point and an upper value lying in said second zone,
   said dilation element having a structure capable of responding to pressure pulses in said pulsating pressure at a frequency of 0.5 to 3 Hz.

2. A dilation device according to claim 1 wherein said catheter is connected to said pressure source by a flexible tube whose radial expandability is substantially less than that of said dilation element.

3. A dilation device according to claim 2 in which said tube is capable of transmitting pressure pulses from said pressure source to the dilation element at a frequency up to about 100 Hz.

4. A dilation device according to claim 1 or 2 in which the catheter is provided with a pressure measuring channel the front end of which extends beyond the dilation element.

5. A dilation device according to claim 1 or 2 in which the expansion characteristic of the dilation element gives a reproducible volume change of the element with a change in the pressure applied.

6. A dilation device according to claim 1 or 2 connected to a pressure source such that the pressure in the dilation element, with each pressure pulse at first increases slowly until the dilation element adjoins the wall of a body cavity and which is recognizable by the diastolic pressure, and the pressure in a pressure recorder, attached to the pressure source, no longer decreases and remains steady.

7. A dilation device according to claim 6 in which the pressure in the pressure container is used for determining the pressure to be adjusted during dilation of the dilation element.

8. In a method for dilating or closing a blood vessel or other body cavity comprising positioning within said vessel or cavity a catheter provided with a radially expandable dilation element having a volume-pressure characteristic including a first zone in which the rate of increase in volume with increasing pressure is relatively low, a second zone in which said rate is substantially higher and substantially linear, and an inflection point separating said first and second zones, and supplying to said dilation element a fluid pressure which periodically fluctuates between a lower limit and an upper limit, the improvement comprising:
   maintaining the lower limit of said fluctuating fluid pressure at a value lying closely below said inflection point and the upper limit thereof at a value within said second zone.

* * * * *